United States Patent [19]

Guest et al.

[11] Patent Number: 5,000,745
[45] Date of Patent: Mar. 19, 1991

[54] HEMOSTATIS VALVE

[75] Inventors: Robert L. Guest; Alexander S. Withers, both of Athens, Tex.

[73] Assignee: Edward Weck Incorporated, Princeton, N.J.

[21] Appl. No.: 273,282

[22] Filed: Nov. 18, 1988

[51] Int. Cl.⁵ .......................................... A61M 25/00
[52] U.S. Cl. .................................. 604/256; 604/167; 251/149.1
[58] Field of Search ............... 604/167, 169, 256, 247, 604/201, 905, 244; 251/149.1; 137/845, 843, 849; 277/207 A, 217, 212 C

[56] References Cited

U.S. PATENT DOCUMENTS

| | | | |
|---|---|---|---|
| 2,937,658 | 5/1960 | Stewart | 137/845 |
| 3,337,124 | 8/1967 | DeMolin et al. | 137/845 |
| 3,459,183 | 5/1966 | Ring et al. | |
| 3,585,996 | 6/1968 | Reynolds et al. | |
| 3,610,279 | 10/1971 | McIntosh | 137/845 |
| 3,659,587 | 5/1972 | Baldwin | |
| 3,825,001 | 6/1974 | Bennet et al. | |
| 3,853,127 | 12/1974 | Spademan | |
| 4,000,739 | 1/1977 | Stevens | |
| 4,177,814 | 12/1979 | Knepshield et al. | |
| 4,244,379 | 1/1981 | Smith | |
| 4,341,239 | 7/1982 | Atkinson | |
| 4,424,833 | 1/1984 | Spector et al. | |
| 4,430,081 | 2/1984 | Timmermans | |
| 4,436,519 | 3/1984 | O'Neill | |
| 4,447,235 | 5/1984 | Clarke | |
| 4,468,224 | 8/1984 | Enzmann et al. | |
| 4,475,548 | 10/1984 | Muto | |
| 4,580,573 | 4/1986 | Quinn | |
| 4,610,665 | 9/1986 | Matsumoto et al. | |
| 4,610,674 | 9/1986 | Suzuki et al. | |
| 4,626,245 | 12/1986 | Weinstein | |
| 4,634,432 | 1/1987 | Kocak | |
| 4,655,752 | 4/1987 | Honkanen et al. | |
| 4,673,393 | 6/1987 | Suzuki et al. | |
| 4,705,511 | 11/1987 | Kocak | |
| 4,723,550 | 2/1988 | Bales et al. | |
| 4,726,374 | 2/1988 | Bales et al. | |
| 4,762,308 | 8/1988 | Geno | 137/849 |
| 4,781,693 | 11/1988 | Martinez et al. | 604/244 |
| 4,809,679 | 3/1989 | Shimonaka et al. | 604/167 |

FOREIGN PATENT DOCUMENTS

| | | | |
|---|---|---|---|
| 3042229 | 5/1982 | Fed. Rep. of Germany | 604/167 |
| 430890 | 6/1911 | France | |

Primary Examiner—John D. Yasko
Assistant Examiner—A. Gutowski
Attorney, Agent, or Firm—Gene Warzecha; Robert E. Lee

[57] ABSTRACT

An introducer sheath assembly having an improved valve assembly including at least three elastic disc shaped membranes. A first membrane has a circular hole through the center to sealingly receive a catheter while a second membrane has a center hole smaller than the hole in the first membrane to sealingly receive a guidewire. The second membrane also has at least one slit through the hole to accommodate passage of the larger catheter through the second membrane. A third membrane contains at least one slit through its center to seal the valve assembly in the absence of a guidewire or catheter.

24 Claims, 8 Drawing Sheets

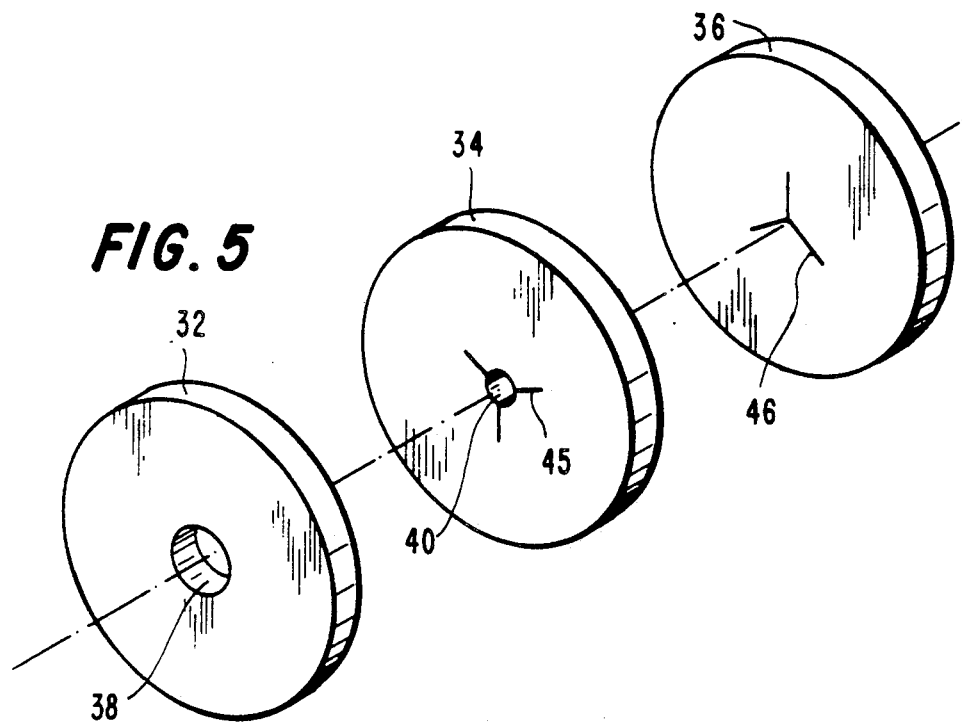
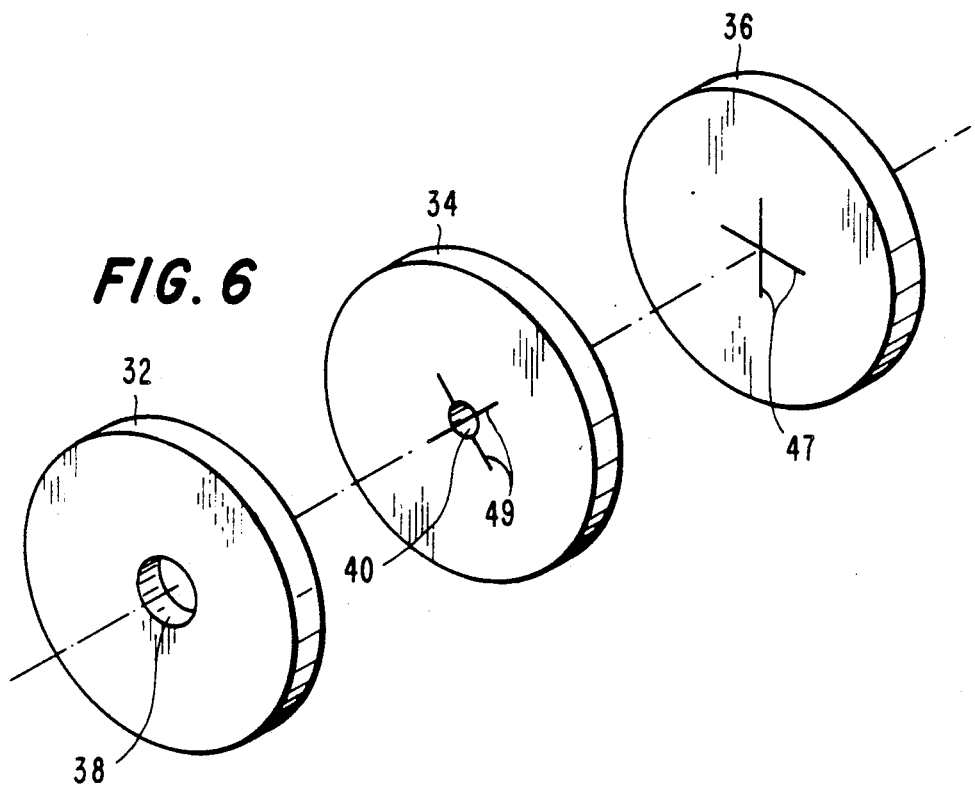

HEMOSTATIS VALVE

BACKGROUND OF THE INVENTION

The present invention relates generally to hemostasis valves and, more particularly, to hemostasis valves for positioning and manipulating intravascular catheters.

It is well known in angiography and cardiac catheterization to use an introducer sheath assembly to provide a passageway to the lumen of a blood vessel through which a catheter can be inserted or removed without blood loss. The introducer sheath assembly typically comprises a body having a valve assembly, the body being coupled to or extending into a flexible cannula which is inserted into the blood vessel cannula usually using a needle, guidewire and dilator. See U.S. Pat. No. 4,000,739. The valve assembly is designed to seal around the catheter when it is in place and to seal off the passage within the introducer sheath assembly when the catheter is withdrawn.

In many procedures followed today it is necessary to use more than one catheter and to exchange one catheter for another which is already in place in the vessel. In such a procedure with the guidewire still in the vessel, the catheter in the body is withdrawn over the guidewire. The guidewire is left within the body through the introducer cannula and introducer valve assembly. The new catheter is inserted through the introducer into the body over the existing guidewire.

In valves having an elastic membrane having a hole therein to accommodate and seal against the catheter, while the guidewire is in place after the first catheter is removed and before the second catheter is inserted, leakage of blood through the introducer valve often occurs since the guidewire has a smaller diameter than the catheter. This is, of course, undesirable.

Other valves for sealing the catheter without using a hole in the membrane and which will accommodate a range of catheter and guidewire diameters are in use but often such designs result in higher frictional forces about the guidewire or catheter being manipulated making it more difficult for the physicians.

It is desirable, therefore, to provide a valve which will provide a good seal when a catheter is present, or with a guidewire alone or when neither the guidewire nor the catheter is present, and which provides relative ease of manipulation of the catheter or guidewire when in use.

SUMMARY OF THE INVENTION

An improved hemostasis valve is provided which includes at least three elastic membranes or disc shaped gaskets A first elastic membrane has a circular hole disposed therein while a second elastic membrane has a hole therein with smaller diameter than the hole in the first membrane. The second membrane also includes at least one slit which intersects the hole. The third membrane contains a slit but no hole. In the preferred embodiment, the slits are straight and when present in the sheath are transverse to each other, preferably at ninety degrees. The slit could be in some other shape, such as Y-shaped, to readily allow the passage of a catheter or guidewire through the membrane. Means are provided for registering the second and third membranes with a transverse slit orientation when present in the valve.

In an alternate embodiment of the valve, a washer with a center aperture is disposed intermediate the second and third membranes. The periphery of the aperture is conically shaped to accommodate opening of the slit in the second membrane distally when a catheter is present.

The valve further comprises a connector means which houses the elastic membranes disposed in a passage extending from an inlet end of the connector to an outlet end. In one embodiment the inlet end and outlet end are adapted to be removably coupled to other devices such as dilators, sepsis preventive devices, cannulae, etc. By way of example a dilator may be positively coupled to the inlet end to facilitate introducing a sheath into the vessel lumen. Once the dilator is removed, a catheter or guidewire can be inserted or removed from the vessel through the valve end sheath without substantial leaking of blood. Alternatively, the inlet end can be configured with a non-coupling cap having an aperture therethrough to receive the catheter and guidewire and a flexible cannula can be permanently attached to the outlet end of the connector means.

In one embodiment the connector means includes a cap portion with the inlet end and a body portion with the outlet end. The cap portion and body portions when attached together compress the peripheries of the membranes therebetween forcing the slit in the third membrane to extend distally away from the second membrane without opening.

Registration of the second and third membrane so that their straight line slits are transverse may be brought about by providing protrusion(s) or indentation(s) on each of the second and third membranes, the protrusions on the second membrane being aligned with respect to the protrusion(s) on the third membrane when their slits are transverse. Recesses are provided within the connector means to receive the protrusions.

BRIEF DESCRIPTION OF THE DRAWINGS

FIG. 5 is an exploded perspective view of an alternate embodiment of the elastic membranes of the hemostasis valve;

FIG. 6 is an exploded perspective view of a second alternate embodiment of the elastic membranes of the hemostasis valve;

DETAILED DESCRIPTION OF THE DRAWINGS

Figure 1:
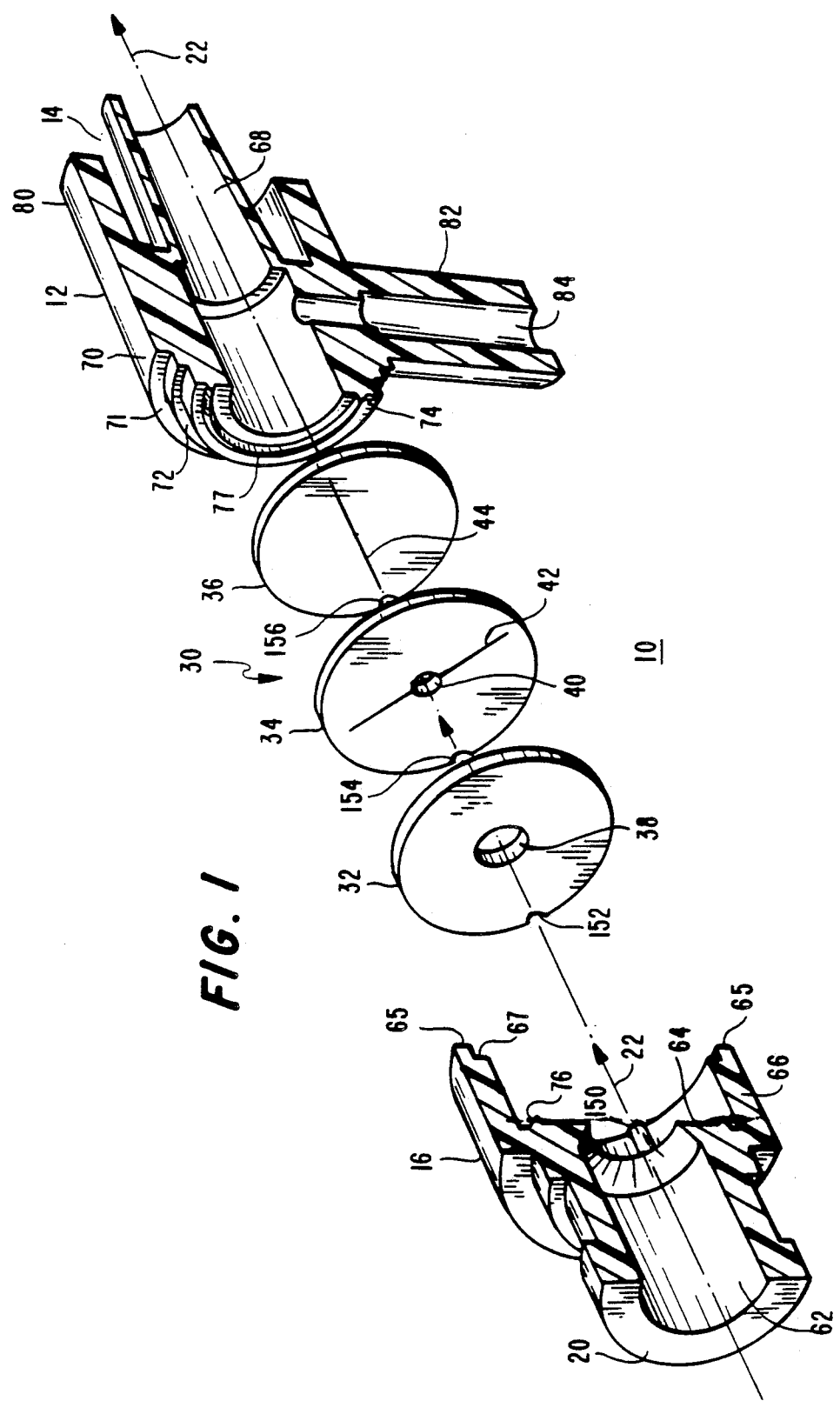
FIG. 1 is an exploded, partially cut away view of an embodiment of the hemostasis valve of the present invention.
Figure 2:
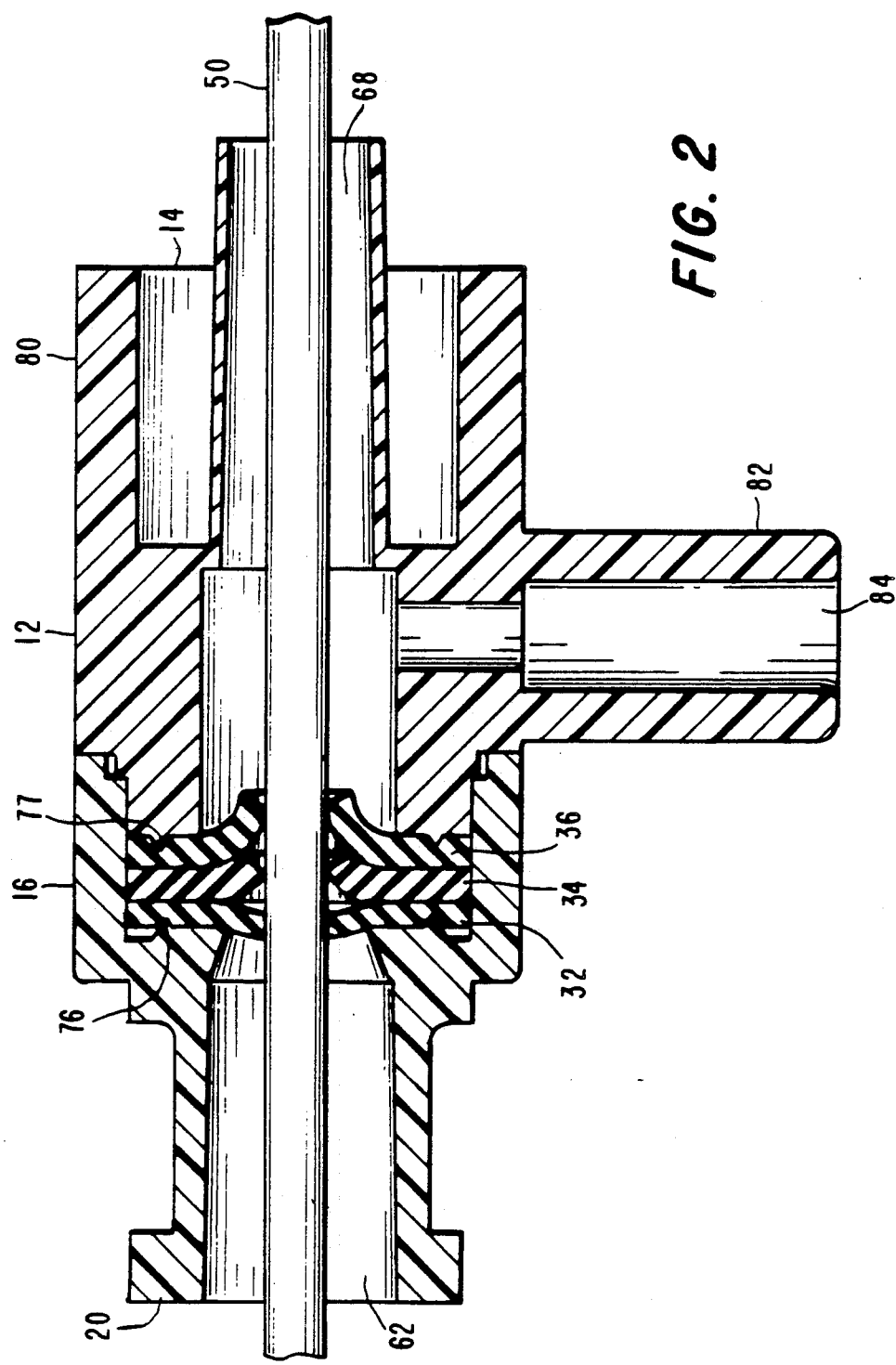
FIG. 2 is an enlarged view in cross section of the embodiment of FIG. 1 with a catheter present in the hemostasis valve.
Figure 3:
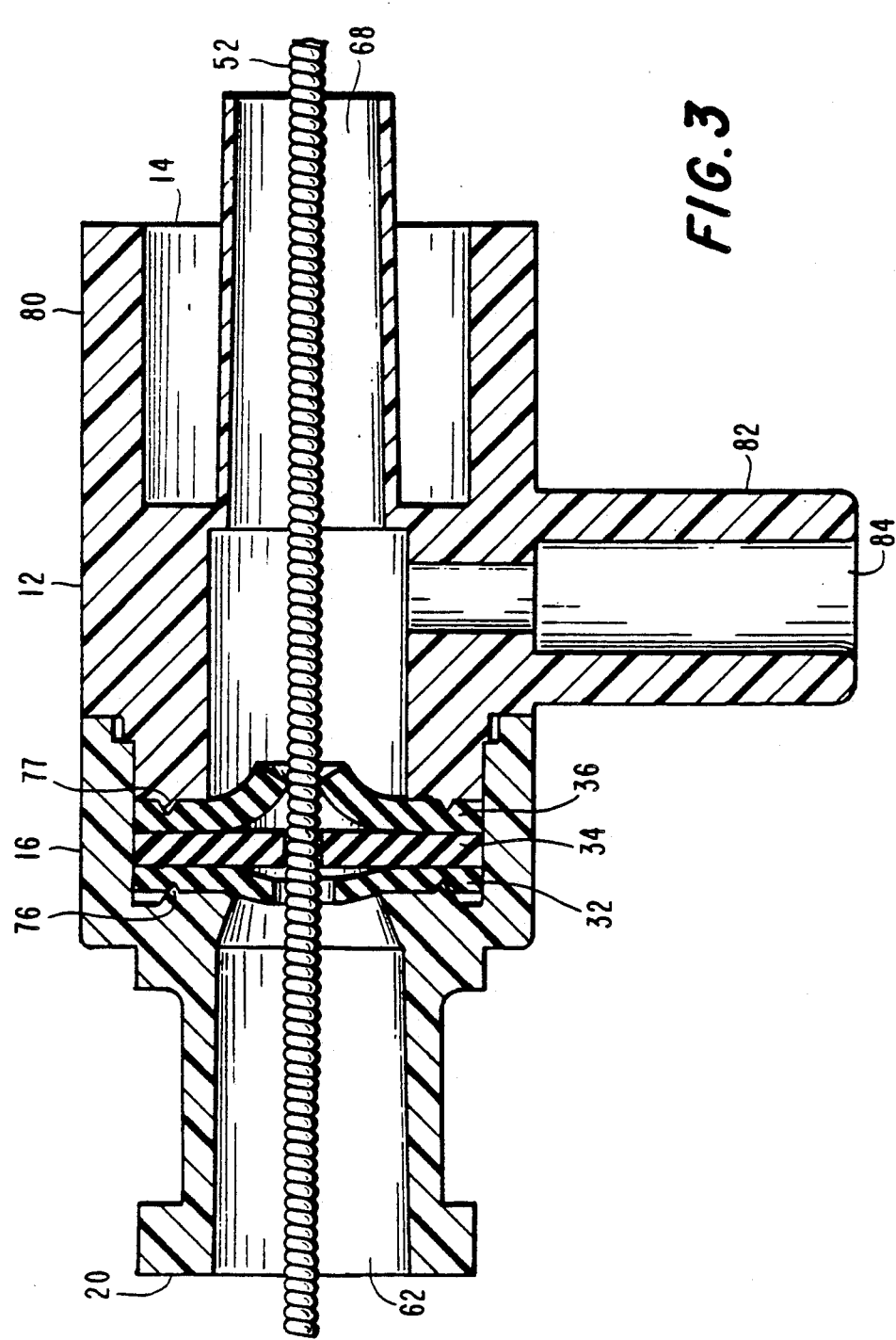
FIG. 3 is an enlarged view in cross section of the embodiment of FIG. 1 with a guidewire present in the hemostasis valve.

Referring now to the FIGS. 1–3, a hemostasis valve designated generally 10 includes a connector having a body 12 with outlet end 14 and a cap 16 connected to the body 12 having an inlet end 20. The connector so formed has a generally cylindrical hollow interior which forms a passage designated by arrow 22 from the inlet end 20 of cap 16 to the outlet end 14 along the axis of the connector. The connector, both cap and body, may be made conveniently of any one of a plurality of well known suitable plastic materials, e.g. high density polyethylene or as used in the preferred embodiment, ABS.

The hemostasis valve further comprises a plurality of elastic membranes designated generally 30 enclosed within the connector and more particularly having at least three elastic membranes 32, 34 and 36.

Each of the membranes is preferably annular in shape and made of latex, silicon rubber or other suitable sealing material. Elastic membrane 32 has a hole 38 located in the center of the membrane. Hole 38 has a diameter slightly smaller than the catheter diameter intended for use with the valve. Elastic membrane 34 has a hole 40 in its center having a diameter slightly smaller than the guidewire diameter intended for use with the catheter. The hole 40 in elastic membrane 34 is substantially smaller than the hole 38 in membrane 32 and when mounted in the valve is coaxial with hole 40. Membrane 34 also has a slit 42, preferably straight which intersects the hole 40 and extends away from the hole diametrically on either side.

Annular elastic membrane 36 has a slit 44 which is preferably straight and passes through the center of the membrane. Preferably the slits 42 and 44 are transverse to one another when housed in the connector, but they need not be. Preferably the slits 42 and 44 are straight but Y-shaped slits 45 and 46 or a pair of crossed slits 49 and 47 could be used as shown in FIGS. 5 and 6, respectively.

The proximal end of the cap 16 has an interior cavity 62 and is in the shape of a female or a modified female luer fitting The cap forms an interior annular recessed ledge 64 at the end of the female luer fitting portion which ledge 64 is at right angles to the passage 22. The cap 16 terminates distally with a cylindrical wall 66 that extends away from the ledge 64 along the passage 22 and terminates in an end surface having an extended annular surface 65 and a recessed annular surface 67.

The end of body 12 which mates with cap 16 is generally cylindrical in shape with an interior cavity 68. The cylindrical wall 70 of body 12 comprises a proximal end surface disposed to be engaged by the cap 16 which end surface includes a recessed annular surface 71 and an extended annular surface 72 adapted to mate with the extended and recessed surfaces 65 and 67, respectively, on cap 16. Wall 70 includes an inner annular end surface 74 which protrudes proximally past the surfaces 65 and 67. The cap 16 may be snapped on or welded or glued to the body 12. When connected together inner annular end surface 74 of the wall 70 and the interior annular recessed ledge 64 retain the peripheral portions of the annular elastic membranes 32, 34, and 36 together to capture them within the cap 16. The disc like membranes are disposed at right angles to the passage 22 and their centers are substantially coaxial with the longitudinal axis of the connector formed by the cap and body.

An annular ridge 76 is present on the ledge 64 and is engaged by the elastic membrane 32 which seals the membrane against the cap. Similarly, an annular ridge 77 is present on surface 74 and is engaged by the membrane 36 which seals the membrane against the body 12.

The distal end 80 of body 12 is also cylindrically shaped in the form of a male luer fitting adapted to receive a flexible cannula with a female luer fitting in such a way that the interior of the body and the passage 22 are in fluid communication with the interior of the flexible cannula.

A cylindrical extension 82 is formed integrally with body 12 and extends laterally away therefrom and contains a passage 84 communicating with the passage 22. This passage can be used to introduce a liquid such as heparinized saline into the hemostasis valve 10. A positive pressure of liquid is maintained throughout use of the valve 10 to prevent blood from flowing through the extension 82.

One manner of application of the valve 10, for example, comprises connecting a hollow plastic dilator (not shown) with a diameter substantially the same as the catheter to the cap 16 with the dilator positioned in the passage 22 and extending beyond the end of the flexible tube coupled to the distal end of the body 12 of the connector. In operation, a hollow needle with a trocar penetrates the vessel and the trocar is removed. A guidewire replaces the trocar the needle is removed and an incision is made in the patient's skin. The dilator with valve 10 attached is introduced over the guidewire until the tapered end of the dilator enters the lumen of the vessel. Next the flexible cannula attached to the valve 10 is introduced to the lumen over the dilator. The guidewire and dilator are removed and the valve and sheath are taped or sutured to the patient. Once the dilator and guidewire are removed, the slit in the membrane 36 closes to seal off the passage 22. The bowed membrane 36 (see FIG. 4, for example) resists the force exerted by the patient's blood pressure and prevents any blood loss. The catheter is now introduced through the hole 38 in membrane 32 and passes through the slits in the membranes 34 and 36 and finally into the lumen of the blood vessel. If it is desired to remove the catheter and insert a new catheter using a guidewire 52 as in a catheter exchange procedure used in coronary angioplasty, the membrane 34 will seal the guidewire when no catheter is present.

When a catheter 50 is inserted through the passage 22, the elastic membrane 32 will sealingly engage the catheter around the hole 38 as shown in FIG. 2. The slits 42 and 44 in the membranes 34 and 36, respectively, open and permit relatively unobstructed passage of the catheter 50 through the membranes. When the catheter 50 is removed, the slit 44 in membrane 36 will close to seal off the holes 38 and 40 preventing any blood flow back through the passage 22.

When the guidewire 52 is inserted through the passage 22 without the presence of catheter 50, the elastic membrane 34 will sealingly engage the guidewire around the hole 40 as shown in FIG. 3. Membrane 32 will provide no obstruction since the hole 38 is larger then the guidewire 52 and the slit 48 in the membrane 36 permits relatively unobstructed passage of the guidewire 52 through the membrane 36. Without the presence of membrane 34, if the catheter 50 were removed and the guidewire left inserted, leakage of blood back through the passage and hole 38 would occur.

Because the slits 42 and 44 in membranes 34 and 36, respectively, are transverse to one another, preferably at 90°, they tend to center the catheter or guidewire in the valve 10. Since the membranes 34 and 36 each contain only a single straight slit they tend to withstand the patient's reverse blood pressure and not open to allow leakage of blood. This is particularly true for the bowed membrane 36.

Figure 10:
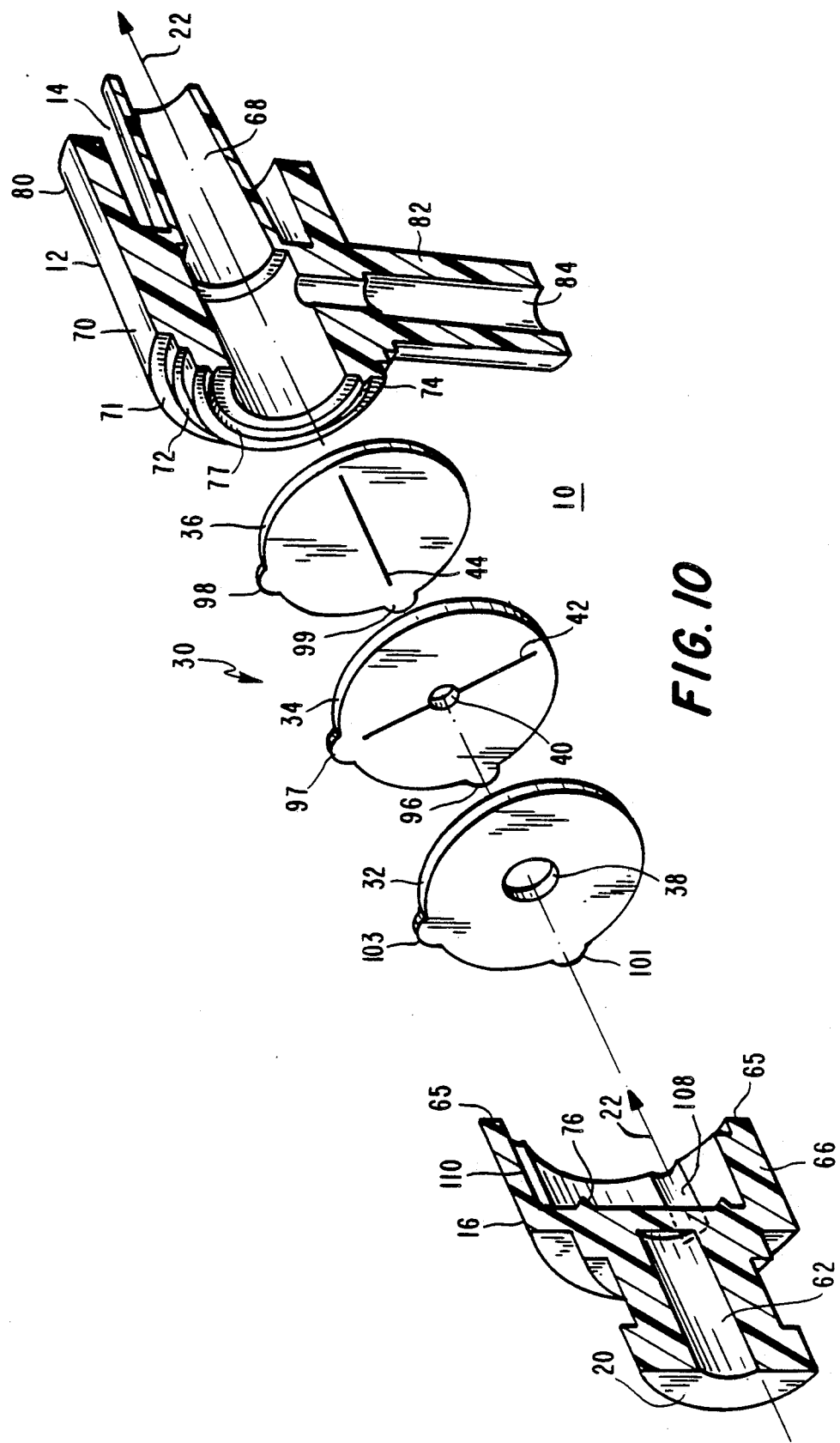
FIG. 10 is an exploded, partially cut away view of a third alternate embodiment of a hemostasis valve.

Referring to FIG. 10, in order to align the slits in the membranes 34 and 36, membrane 34 includes two protruding ears 96 and 97 on its periphery while membrane 36 includes two protruding ears 98 and 99. The ears are separated by 90° on each membrane and the pair of ears 96, 97 of membrane 34 are aligned with the pair 98, 99 on membrane 36.

Membrane 32 is also shown with ears 101 and 103 aligned with ears 96 and 97 on membrane 34 but it is not necessary that membrane 32 contain protruding ears. Corresponding recesses are formed within the cylindrical walls of the cap to accommodate the membranes. In FIG. 10 only a one quarter section of the cap is shown and it exposes a portion of recess 108 and recess 110 in the interior of the cap. Other means for aligning the membranes in the cap could be used, such as forming recesses in the membranes and molding protrusions in the cap or forming notches, etc. For example, in FIG. 1 by way of illustration a protrusion 150 is present on the interior surface of cylindrical wall 66 of cap 16. Corresponding indentations 152, 154 and 156 are present on the membranes 32, 34 and 36, respectively, to accommodate the protrusion when assembled within the valve.

While it has been described above to have the slits transverse to one another it is not necessary. They could be otherwise aligned and the valve assembly will still function properly.

Figure 4:
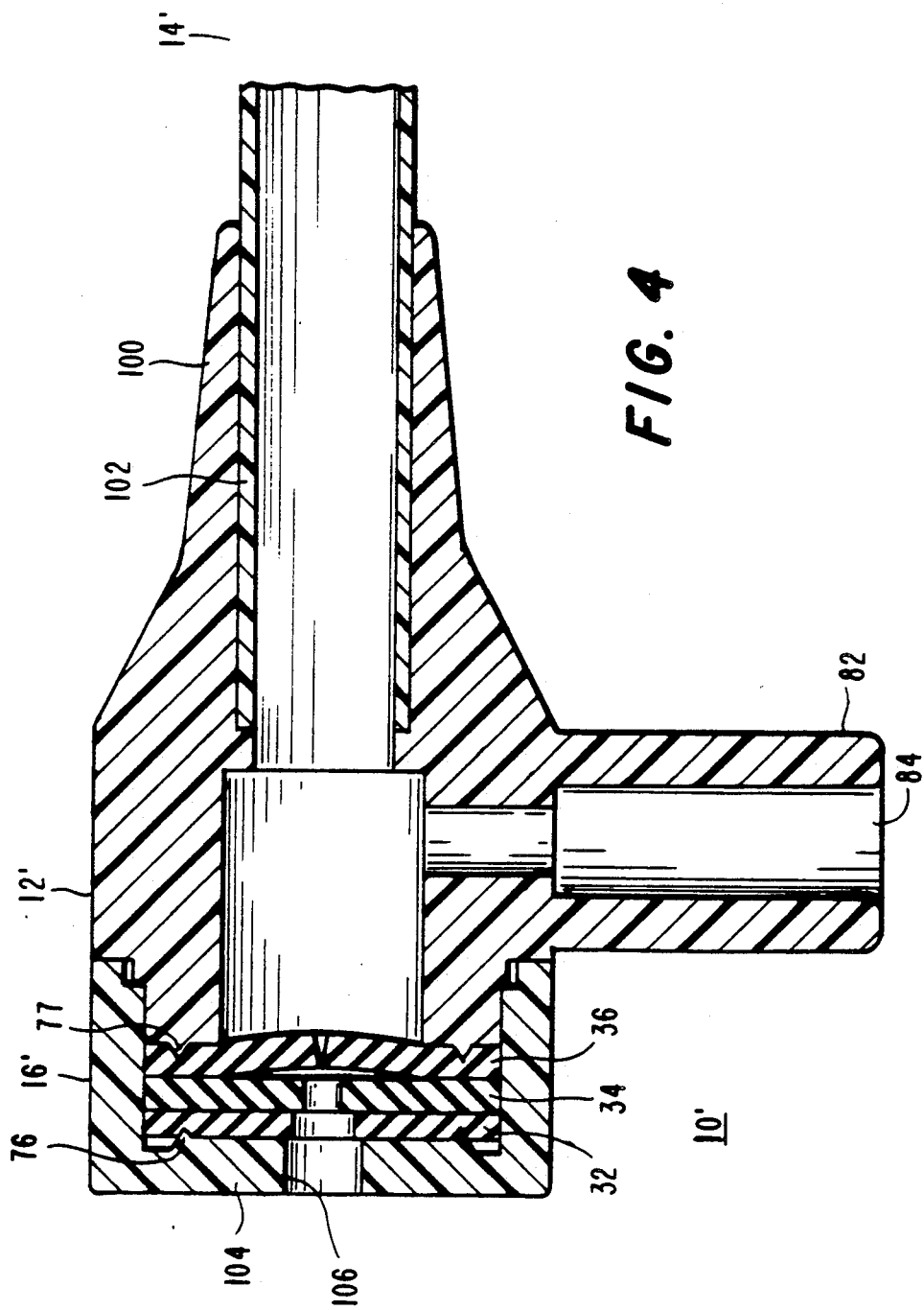
FIG. 4 is an enlarged view in side elevation cross section of the hemostasis valve used in an introducer sheath assembly.

Referring now to FIG. 4 a valve generally 10' is shown with a connector having a body 12' with outlet end 14' and a cap 16' connected to the body 12'. Except for its distal end, the body 12' is identical to body 12. In place of the male luer fitting integrally formed with body 12, body 12' comprises a tapered portion 100 encircling a length of flexible cannula 102. Similarly, cap 16' is identical to cap 16, except for its proximal portion. In place of the female luer fitting, connecting portion cap 16' comprises an end wall 104 having an aperture 106 therethrough. The valve 10' includes the membranes 30 of FIGS. 1-3. The assembly of FIG. 4 provides for an introducer sheath assembly having a hemostasis valve.

In order to insure a good seal between the annular ridge 76 and the membranes and between the annular ridge 77 and the membranes the membranes are squeezed with a good deal of pressure. This forces the end membranes 32 and 36 to bow outwardly from the center membrane 34. See FIGS. 2 and 3 which show the bowing of membrane 32 proximally and FIG. 4 which shows the bowing of membrane 36 distally. It does not bow so much as to open the slit completely but the convex bowing resists any back pressure from the vessel to force blood back through the passage 22. The stronger the back force the more the tendency for the slit to close. Bowing of membrane 36 occurs for all of the embodiments shown in the Figures.

Figure 7:
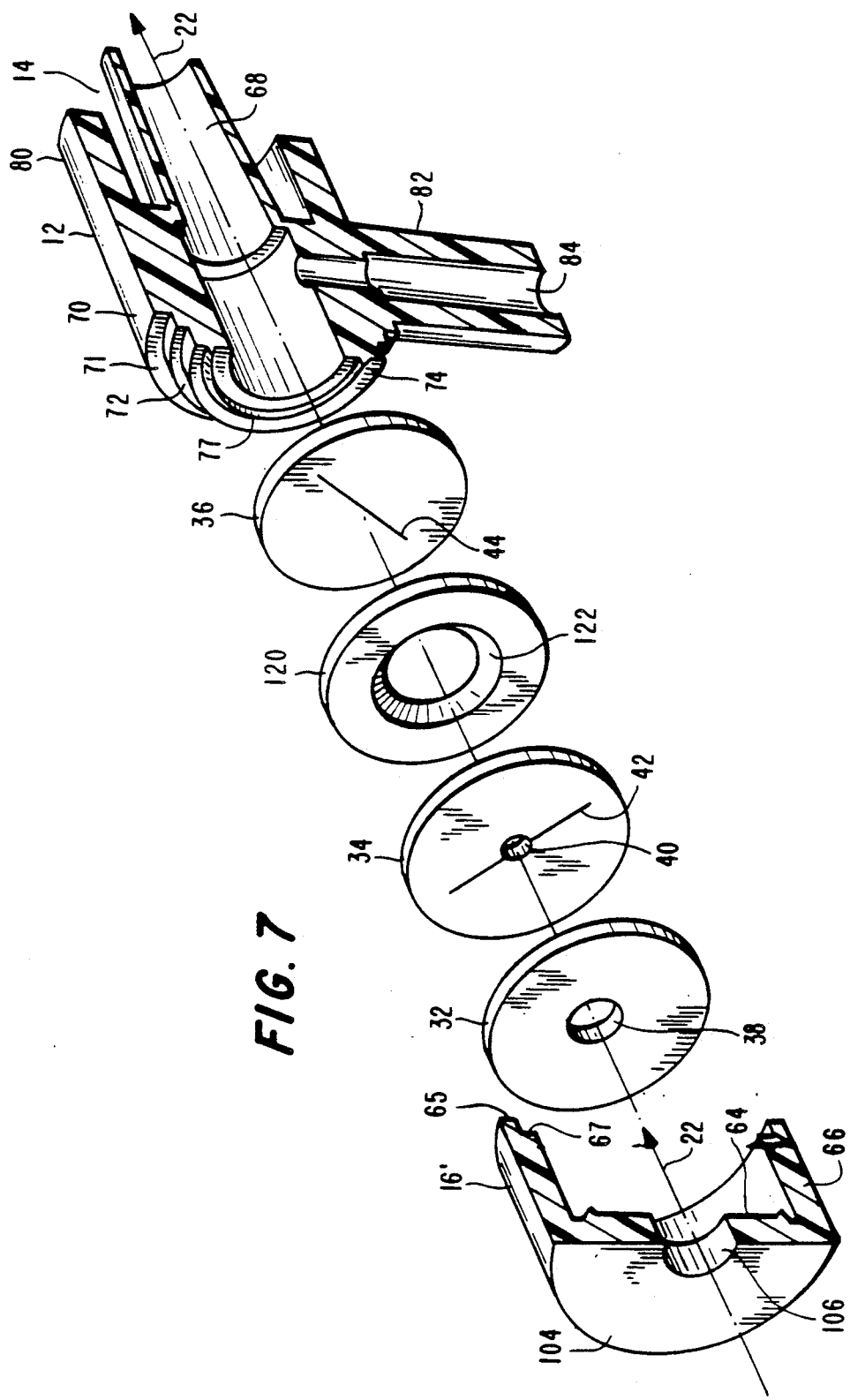
FIG. 7 is an exploded perspective view in cross section of a second alternate embodiment of the hemostasis valve of FIG. 1.
Figure 8:
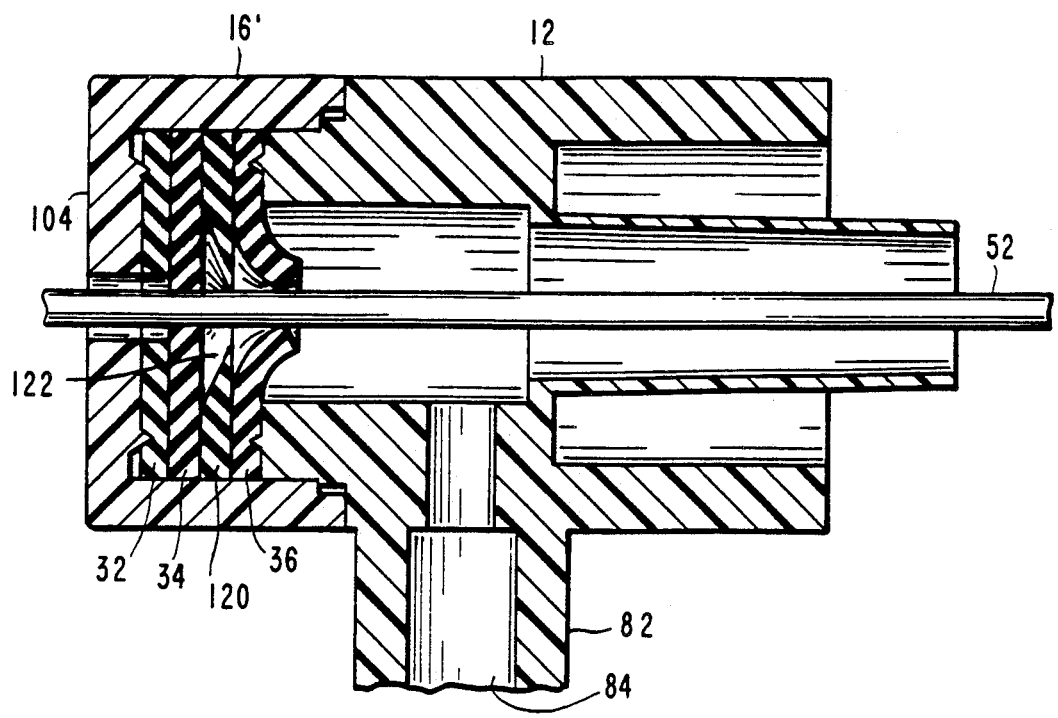
FIG. 8 is an enlarged side elevational view in cross section of the hemostasis valve of FIG. 7 with a guidewire present.
Figure 9:
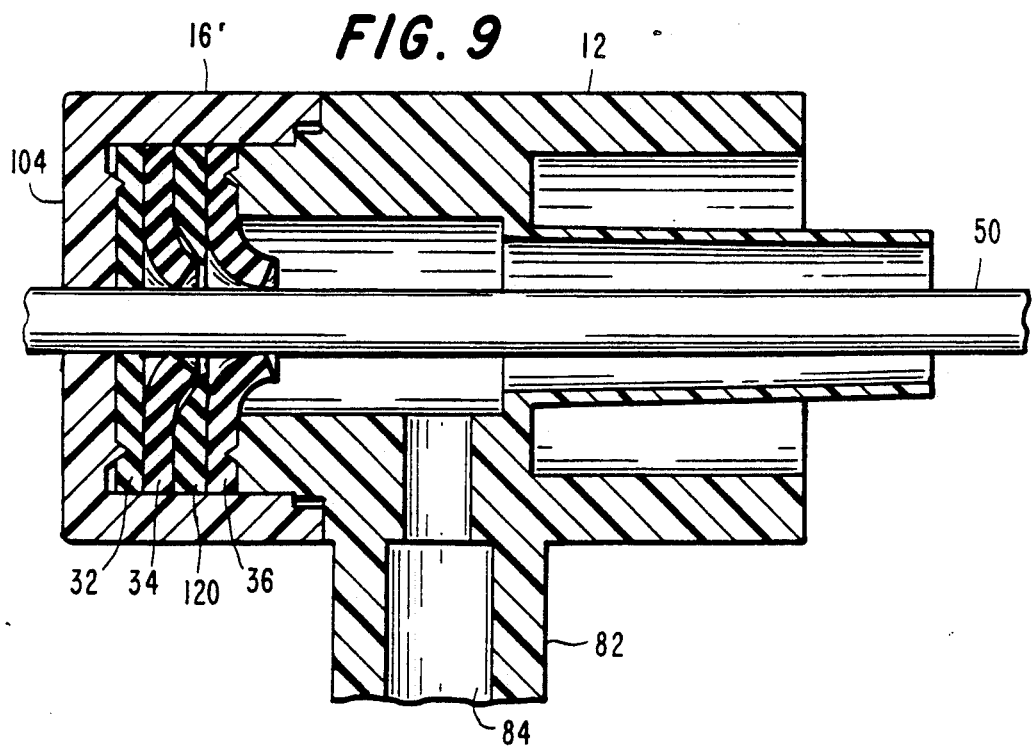
FIG. 9 is an enlarged side elevational view in cross section of the the hemostasis valve of FIG. 7 with a catheter present.

FIG. 7 is an alternate embodiment introducer sheath assembly which includes body 12, cap 16' and the valve assembly membranes 32, 34 and 36. It also includes an annular washer 120 disposed intermediate membrane 34 and membrane 36 with membrane 36 located distally of membrane 34 and washer 120. The washer 120 includes a large center opening 122. In the preferred embodiment the opening 122 is conically shaped with the larger aperture in the side adjacent membrane 34. As shown in FIG. 9, when a catheter is present throughout the smaller opening and slit in membrane 34 it causes a portion of membrane material to be pushed distally in the direction of membrane 36. The conically shaped aperture 122 in washer 120 provides a space to accommodate the displaced material of membrane 34 so that it does not engage membrane 36 and cause any unwanted interference or increased resistance or friction to the movement of catheter 50 back and forth through the assembly. Compare with FIG. 2.

While the present invention has been disclosed in connection with the preferred embodiment thereof, it should be understood that there may be other embodiments which fall within the spirit and scope of the invention as defined by the following claims.

What is claimed is:

1. In a hemostasis valve, the improvement comprising:
   a first planar elastic membrane having a circular hole disposed therein;
   a second planar elastic membrane having a circular hole with a diameter smaller than said circular hole in said first elastic membrane, said second elastic membrane further comprising at least one slit which intersects said smaller hole, said slit aligned in a single plane extending through said elastic membrane; and
   a third planar elastic membrane with no hole having at least one slit therein.

2. The hemostasis valve of claim 1 wherein said holes in said first and second elastic membranes are substantially coaxial.

3. The hemostasis valve of claim 2 wherein said at least one slit in said second elastic membrane lies along a substantially straight line in a first direction and said at least one slit in said third elastic membrane lies along a substantially straight line in a direction transverse to said first line, said slits intersecting the common coaxial center line of said first and second membrane.

4. The hemostasis valve of claim 3 wherein said slit in said second and third elastic membranes are substantially at right angles to one another.

5. The hemostasis valve of claim 3 wherein said valve comprises means for registering said second and third elastic membranes in said assembly whereby said slits are transverse to one another.

6. The hemostasis valve of claim 5 wherein said membranes are circular and said registering mean comprises a pair of spaced apart protruding ears on each of said second and third membranes, said pair of ears or said second membrane aligned with said pair on said third membrane.

7. The hemostasis valve of claim 1 wherein said valve further comprises a washer disposed adjacent to and between said second and third membranes and having an aperture disposed therein which is larger than and overlaps said hole in said second membrane.

8. The hemostasis valve of claim 7 wherein the periphery of said aperture in said washer is conically shaped to accommodate separation of said one slit in said second membrane distally when a catheter is present in said valve assembly 9. A hemostasis valve comprising:

connector means having an inlet end, an opposite outlet end, and a passage through said valve extending from said inlet end to said outlet end;

a plurality of elastic membranes mounted in said passage, said plurality comprising:

a first planar elastic membrane having a circular hole disposed therein;

a second planar elastic membrane having a circular hole with a diameter smaller than said circular hole in said first elastic membrane said second elastic membrane further comprising at least one slit which intersects said smaller hole, said slit aligned in a single plane extending through said elastic membrane; and a third planar elastic membrane having at least one slit therein.

10. This hemostasis valve of claim 9 wherein said holes in said first and second elastic membranes are substantially coaxial.

11. The hemostasis valve of claim 10 wherein said at least one slit in said second elastic membrane lies along a substantially straight line in a first direction and said at least one slit in said third elastic membrane lies along a substantially straight line in a direction transverse to said first line, said slits intersecting the common coaxial center line of said first and second membranes.

12. The hemostasis valve of claim 11 wherein said slit is said second and third elastic membranes are substantially at right angles to one another.

13. The hemostasis valve of claim 11 wherein said valve comprises means for registering said second and third elastic membranes in said assembly whereby said slits are transverse to one another.

14. The hemostasis valve of claim 9 wherein said connector means comprises a second inlet in fluid communication with said passage.

15. The hemostasis valve of claim 9 wherein said inlet end comprises a coupler means for removably coupling said valve to a separate medical device.

16. The hemostasis valve of claim 15 wherein said coupler means comprises a female luer coupling.

17. The hemostasis valve of claim 9 wherein said outlet end comprises a coupler means for removably coupling said valve to a sheath cannula assembly.

18. The hemostasis valve of claim 17 wherein said coupler means comprises a male luer coupling.

19. The hemostasis valve of claim 9 wherein said valve comprises a flexible cannula fluidly connected to said outlet end.

20. The hemostasis valve of claim 9 wherein said connector means comprises a cap portion having said inlet end for coupling to a body portion having said outlet end, said cap and body portions adapted to compress the peripheral portions of said first, second and third elastic membranes together when said cap and body portions are coupled together, the center portion of said third elastic membrane having said slit being displaced distally from said second elastic membrane by said compression without opening said slit.

21. The hemostasis valve of claim 9 wherein said at least one slit in said second and third membranes comprise Y-shaped slits 22. The hemostasis valve of claim 9 wherein said at least one slit of said second membrane comprises a pair of slits transverse to one another intersecting said hole.

23. The hemostasis valve of claim 22 wherein said at least one slit of said third membrane comprises a pair of slits transverse to one another.

24. The valve of claim 13 wherein said membranes are circular and said registering means comprises a pair of spaced apart protruding ears on each of said second and third membranes, said pair on said second membrane being aligned with said pair on said third membrane; and said connector means comprising an internal recess to receive said protruding ears.

* * * * *